United States Patent [19]
Wilk

[11] Patent Number: 5,385,528
[45] Date of Patent: Jan. 31, 1995

[54] INTRAPERICARDIAL ASSIST DEVICE AND ASSOCIATED METHOD

[76] Inventor: Peter J. Wilk, 185 W. End Ave., New York, N.Y. 10023

[21] Appl. No.: 78,567

[22] Filed: Jun. 17, 1993

[51] Int. Cl.⁶ ............................................. A61B 17/12
[52] U.S. Cl. ...................................... 600/18; 601/153; 604/99
[58] Field of Search .................. 128/898; 600/16, 17, 600/18; 604/96, 97, 98, 99; 601/153, 152, 151

[56] References Cited

U.S. PATENT DOCUMENTS 5,171,297 12/1992 Barlow et al. ......................... 604/96
5,195,970 3/1993 Gahara .................................. 604/96

*Primary Examiner*—William E. Kamm
*Assistant Examiner*—Scott M. Getzow
*Attorney, Agent, or Firm*—R. Neil Sudol; Henry D. Coleman

[57] ABSTRACT

In a surgical method for resuscitating a stopped heart an inflatable balloon is inserted in a folded, collapsed configuration into an intrapericardial space about the stopped heart. The balloon is inflated in the intrapericardial space to place a compressive pressure on the stopped heart sufficient to force blood from the heart.

21 Claims, 2 Drawing Sheets

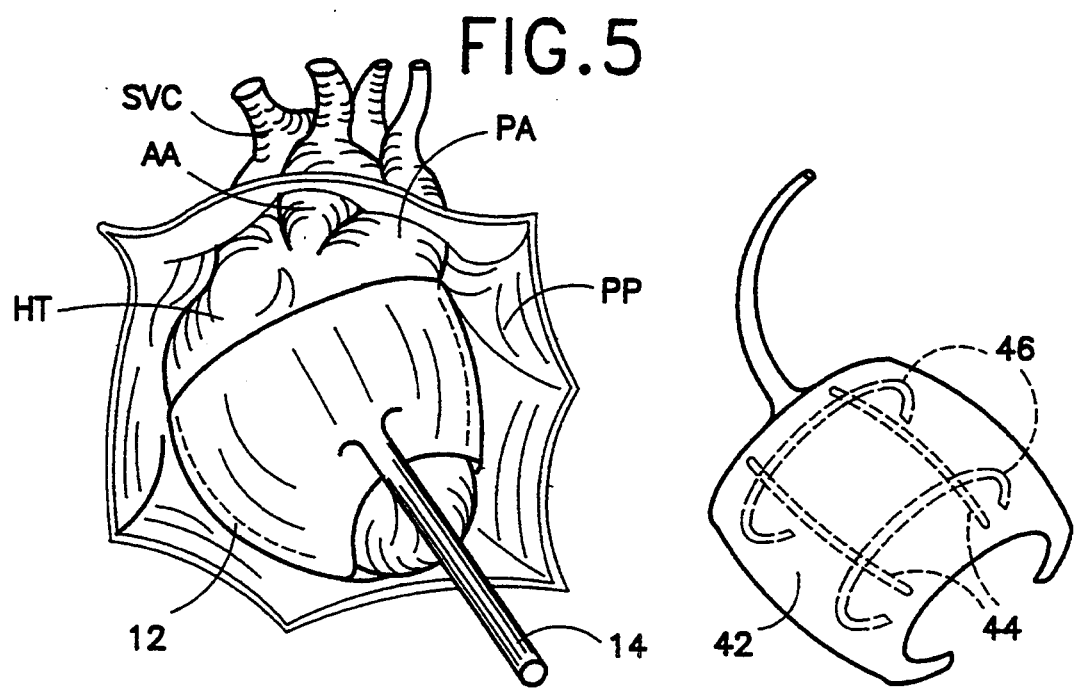
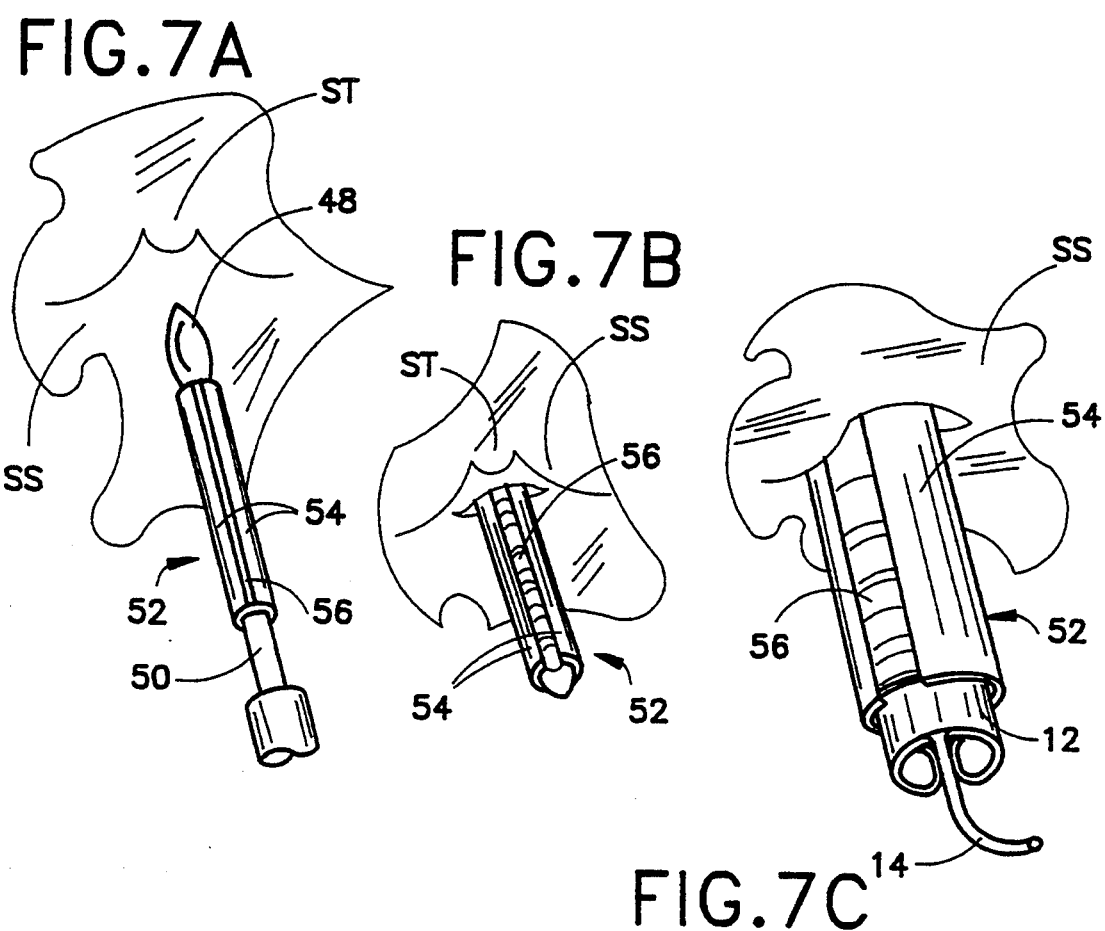

INTRAPERICARDIAL ASSIST DEVICE AND ASSOCIATED METHOD

BACKGROUND OF THE INVENTION

This invention relates to an intrapericardial assist device. This invention also relates to an associated surgical method for starting a stopped heart.

When a patient's heart stops, for example, in the operating room, cardiopulmonary resuscitation (CPR) is required. In that procedure the chest is violently pounded at the region of the sternum to compress the chest and thereby compress the heart between the sternum and the spine. This compression forces blood out of the ventricles through the one-way valves of the heart. When the pressure on the heart is released, the heart expands and blood is sucked into the heart.

For all its violence, CPR is a delicate procedure in that it must be performed correctly in order to have the desired result of starting the stopped heart. A problem with CPR is that, whether or not it is performed correctly, CPR often results in cracked ribs, a fractured sternum and destroyed costochondral (cartilage) junctions. Thus even if a patient survives CPR, he is often injured.

It is known to insert a needle into the intrapericardial space around the heart. This procedure is frequently undertaken to obtain a sample of fluid (e.g., blood) in the intrapericardial space. An electrical sensor at the tip of the needle senses when the surface of the heart has been reached and alerts the doctor to cease pushing on the needle.

OBJECTS OF THE INVENTION

An object of the present invention is to provide a method and/or an associated device for resuscitating a stopped heart.

A more particular object of the present invention is to provide such a method wherein the excessive trauma characteristic of conventional CPR is largely, if not completely, obviated.

Another object of the present invention is to provide such a method which is easy and quick to use.

Another, more particular, object of the present invention is to provide such a method which may be implemented at least partially automatically, thereby reducing the exertion required by the resuscitating personnel.

A further particular object of the present invention is to provide a device for cardiopulmonary resuscitation.

These and other objects of the present invention will be apparent from the drawings and detailed descriptions herein.

SUMMARY OF THE INVENTION

A surgical method for resuscitating a stopped heart comprises, in accordance with the present invention, the steps of providing an inflatable balloon in a collapsed configuration, inserting the balloon into an intrapericardial space about a stopped heart, and inflating the balloon in the intrapericardial space to place a compressive pressure on the stopped heart sufficient to force blood from the heart.

According to another feature of the present invention, insertion of the balloon is accomplished by providing a hypodermic type needle, inserting the needle through a skin surface face and into the intrapericardial space, and injecting the balloon in the collapsed configuration into the intrapericardial space. The collapsed balloon may be inserted into the intrapericardial space through the needle itself or through a dilating device which is introduced partially into the intrapericardial space via the needle.

Generally, the balloon is in the form of a cuff which is folded partially around itself in the collapsed, insertion configuration. Then, the balloon is unfolded upon insertion of the balloon into the intrapericardial space. Upon unfolding, the balloon is partially wrapped about the heart.

According to a further feature of the present invention, the balloon is periodically inflated and deflated until the heart begins pumping of its own accord. The periodic inflation of the cuff may be implemented at least partially automatically by having the balloon connected to a periodically activated pressurization device. That device may be provided with setting knobs for varying the rate and pressure applied to the cuff upon proper disposition thereof in the intrapericardial space about the heart.

An intrapericardial assist device comprises, in accordance with the present invention, a balloon having a configuration of a cuff in an expanded configuration, the balloon having a predetermined size and shape in the expanded configuration so that the balloon is capable of being disposed in an intrapericardial space about a stopped heart. The balloon is provided with a spring connected to the balloon for automatically unfurling the balloon from a folded collapsed configuration to an unfolded collapsed configuration. In addition, an inflation element different from the spring is operatively connected to the balloon for inflating the balloon from the unfolded collapsed configuration to an unfolded expanded configuration.

The spring means may take the form of one or more elongate rib elements.

As discussed hereinabove, the inflation element may include a device for automatically and periodically inflating and alternately deflating the balloon upon a disposition thereof into the intrapericardial space.

The balloon or inflatable cuff is generally provided in a prepackaged folded and collapsed configuration already inserted, for example, into a hypodermic type needle provided at its distal end with an electrical sensor for detecting the surface of the heart. Alternatively, the balloon or cuff may be inserted in its folded and collapsed configuration into a dilating device which has a distal end positioned in the intrapericardial space.

Accordingly, a specific surgical method for resuscitating a stopped heart comprises, in accordance with the present invention, the steps of providing a hypodermic type needle and an inflatable balloon in a collapsed configuration, partially inserting the needle into an intrapericardial space about a stopped heart, inserting the balloon into the intrapericardial space through the needle, and inflating the unfolded balloon in the intrapericardial space to place a compressive pressure on the stopped heart sufficient to force blood from the heart.

Alternatively, a surgical method for resuscitating a stopped heart comprises the steps of (a) providing a hypodermic type needle with a dilating device, (b) further providing an inflatable balloon in a collapsed configuration, (c) partially inserting the needle with the dilating device into an intrapericardial space about a stopped heart, (d) removing the needle from the intrapericardial space while maintaining a distal end portion of the dilating device in the intrapericardial space, (e)

upon disposition of the distal end portion of the dilating device in the intrapericardial space, expanding the dilating device, (f) inserting the balloon in the collapsed configuration into the intrapericardial space through the expanded dilating device, and (g) inflating the unfolded balloon in the intrapericardial space to place a compressive pressure on the stopped heart sufficient to force blood from the heart.

A method in accordance with the present invention solves the problem of the trauma and injury inflicted upon a patient during conventional CPR. Ribs and sternum remain intact.

BRIEF DESCRIPTION OF THE DRAWING

FIG. 5 is a perspective view of the cuff of FIGS. 1-4 in an expanded configuration in place inside an intrapericardial space.

FIG. 6 is another schematic perspective view of an inflatable intrapericardial cuff in accordance with the present invention, showing memory ribs inside the cuff for aiding in an unfolding thereof upon insertion of the cuff into an intrapericardial space.

FIGS. 7A-7C are schematic perspective views showing successive steps in one intrapericardial cuff insertion procedure in accordance with the present invention.

DETAILED DESCRIPTION

Figure 1:
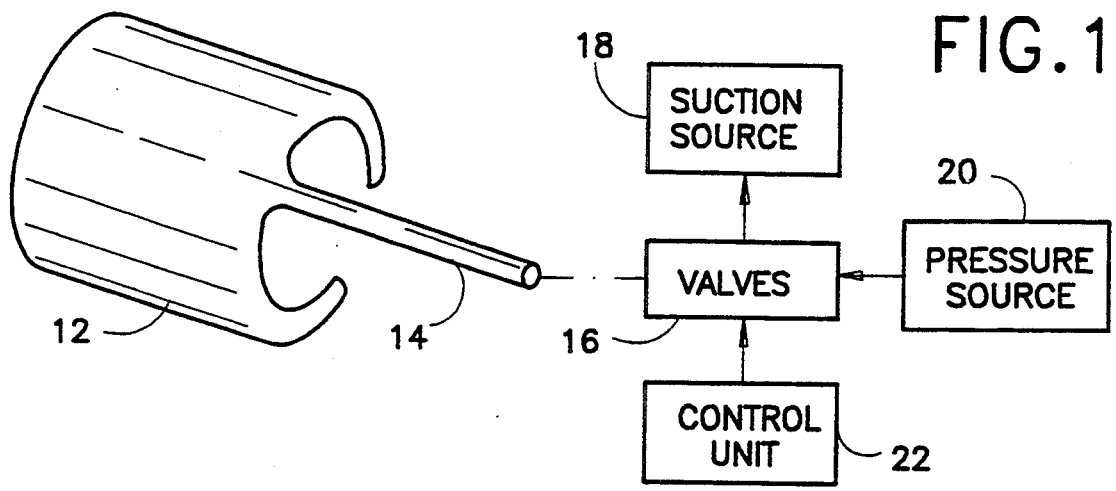
FIG. 1 is a partially a schematic perspective view, on a reduced scale, and partially a block diagram of an intrapericardial assist or resuscitation assembly in accordance with the present invention, showing an inflatable intrapericardial cuff in an expanded configuration.

As illustrated in FIG. 1, an intrapericardial assist or resuscitation assembly comprises an alternately inflatable and collapsible balloon 12 in the form of a cuff. Cuff 12 has an elongate tube 14 extending to a valve device 16 which is connected to a suction source or vacuum generator 18 and to a source 20 of pressurized fluid such as water, saline solution or a gas such as air. In response to signals from a control unit 22, valve device 16 periodically connects cuff 12 to pressure source 20 and alternately to suction source 18, whereby cuff 12 is rapidly and forcefully inflated with a predetermined periodicity.

Control unit 22 may be provided with setting knobs (not illustrated) for varying the rate and maximum pressure that is applied to the cuff upon proper disposition thereof in the intrapericardial space about the heart.

Figure 2:
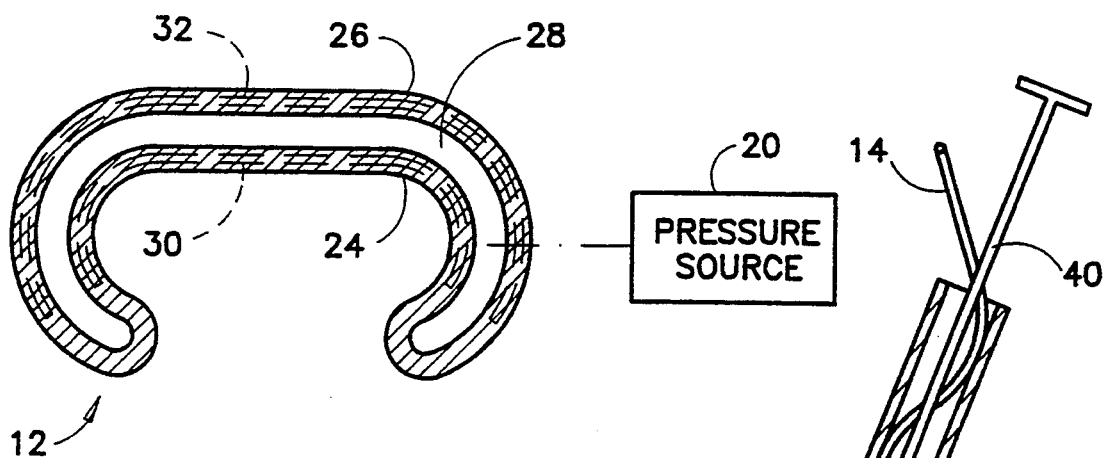
FIG. 2 is a schematic cross-sectional view of the inflatable intrapericardial cuff of FIG. 1.

As illustrated in FIGS. 1 and 2, cuff 12 has an arcuate, generally C-shaped configuration in its expanded or inflated state. Cuff 12 has a pair of major C-shaped walls 24 and 26 defining a pressurization chamber 28. Embedded in walls 24 and 26 are spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure.

Figure 3:
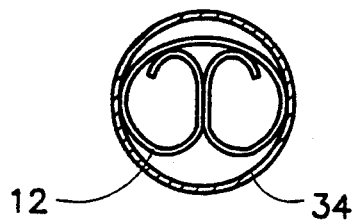
FIG. 3 is a schematic transverse cross-sectional view of the inflatable intrapericardial cuff of FIGS. 1 and 2 in a folded, collapsed pre-insertion configuration inside a hypodermic type needle.
Figure 4:
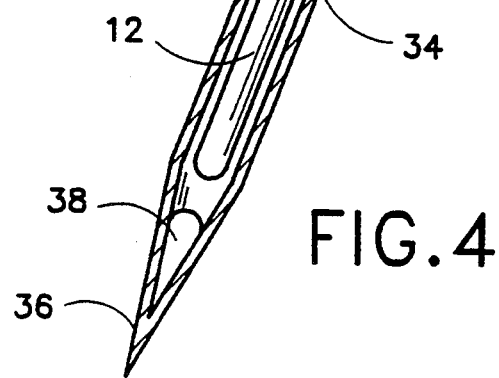
FIG. 4 is a schematic longitudinal cross-sectional view of the inflatable intrapericardial cuff of FIGS. 1-3 in the folded, collapsed pre-insertion configuration inside the hypodermic needle of FIG. 3.

As illustrated in FIGS. 3 and 4, prior to a cardiopulmonary resuscitation procedure, cuff 12 is folded and inserted in a collapsed configuration inside a hollow hypodermic type needle 34. Needle 34 is provided at a distal end 36 with an aperture 38 for the ejection of folded and collapsed cuff 12 by a distally directed stroke of a plunger member 40 upon a disposition of distal end 36 into an intrapericardial space during a cardiopulmonary resuscitation procedure. Distal end 36 is also provided with an electrical sensor for detecting the surface of the heart, as is conventional in known intrapericardial sampling needles.

Distal end 36 of intrapericardial needle 34 is inserted into the intrapericardial space through the skin under the patient sternum.

FIG. 5 shows the placement of cuff 12 in an intrapericardial space between a heart HT and the associated surrounding parietal pericardium PP. The diagram also shows the superior vena cava SVC, the pulmonary artery PA, the ascending aorta AA, and other veins and arteries.

As depicted in FIG. 6, an inflatable intrapericardial cuff 42 may be provided with a plurality of longitudinally extending ribs 44 and a plurality of transversely extending expansion ribs 46. Each rib 46 has a memory whereby the rib may be bent for insertion and retrieval from a patient's intrapericardial space, but tends to assume a pre-established configuration (FIG. 6) upon insertion of the cuff 42 into an intrapericardial space or cavity.

In another cuff insertion procedure depicted in FIGS. 7A-7C, a sharp distal tip 48 of an intrapericardial needle 50 is inserted through a patient's skin SS under the sternum ST. A dilating device 52 comprising a plurality of longitudinal ribs 54 interconnected by stretchable membranes 56 surrounds needle 50 during the insertion procedure. Upon the insertion of distal tip 48 into the intrapericardial cavity at the patient's heart, dilating device is slid in the distal direction so that a distal end portion thereof is disposed or inserted into the intrapericardial cavity. Needle 50 is then removed, as shown in FIG. 7B.

Upon the removal of needle 50 from the patient, leaving dilating device 52 partially inserted into the patient's intrapericardial cavity, the dilating device may be expanded, for example, by the insertion of a series of increasing large elongate rigid dilators (not shown). Then, cuff 12 or 42 is inserted in a folded collapsed configuration into the intrapericardial cavity through the expanded dilating device 52, as shown in FIG. 7C. An inserter (not illustrated) may be used for pushing the cuff through dilating device 52.

The general use and structure of dilating device 52 is described in detail in allowed U.S. patent application Ser. Nos. 851,097 filed Mar. 13, 1992 and 893,991 filed Jun. 5, 1992. The disclosures of those applications are hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method for resuscitating a stopped heart, comprising the steps of:
   providing an inflatable balloon in a collapsed configuration;
   inserting said balloon into an intrapericardial space about a stopped heart;
   inflating said balloon in said intrapericardial space to place a compressive pressure on the stopped heart sufficient to force blood from the heart; and
   subsequently no said step of inflating, deflating said balloon to permit blood to re-enter the heart.

2. The method defined in claim 1 wherein said step of inserting includes the steps of providing a hypodermic type needle, inserting said needle through a skin surface and into said intrapericardial space, and injecting said balloon in said collapsed configuration into said intrapericardial space.

3. The method defined in claim 2, further comprising the step of again inflating said balloon upon deflation thereof.

4. The method defined in claim 1, further comprising the step of periodically inflating said balloon upon completion of said step of inserting.

5. The method defined in claim 4 wherein said balloon is connected at a proximal end to a pressurization device, said step of periodically inflating including the step of operating said pressurization device.

6. The method defined in claim 1 wherein said balloon has an arcuate cuff configuration in an inflated configuration, further comprising the step of placing said balloon at least partially around the heart in said intrapericardial space upon completion of said step of inserting.

7. The method defined in claim 1, further comprising the steps of providing a hypodermic type needle and a dilating device, said step of inserting including the steps of partially inserting said needle through a skin surface and into said intrapericardial space and placing a distal end portion of said dilating device into said intrapericardial space via said needle upon the partial insertion thereof into said intrapericardial space, also comprising the step of expanding said dilating device upon the insertion of the distal end portion thereof into said intrapericardial space, said balloon being inserted into said intrapericardial space through the expanded dilating device.

8. An intrapericardial assist device comprising;
   a balloon having a configuration of a cuff in an expanded configuration, said balloon having a predetermined size and shape in said expanded configuration so that said balloon is capable of being disposed in an intrapericardial space about a stopped heart;
   spring means connected to said balloon for automatically unfurling said balloon from a folded collapsed configuration to an unfolded collapsed configuration; and
   inflation means different from said spring means and operatively connected to said balloon for inflating said balloon from said unfolded collapsed configuration to an unfolded expanded configuration.

9. The device defined in claim 8 wherein said spring means includes an elongate rib element.

10. The device defined in claim 8 wherein said inflation means includes means for automatically and periodically inflating and alternately deflating said balloon upon a disposition thereof into said intrapericardial space.

11. A surgical method for resuscitating a stopped heart, comprising the steps of:
    providing a hypodermic type needle and an inflatable balloon in a collapsed configuration;
    partially inserting said needle into an intrapericardial space about a stopped heart;
    inserting said balloon into said intrapericardial space through said needle;
    inflating the unfolded balloon in said intrapericardial space to place a compressive pressure on the stopped heart sufficient to force blood from the heart; and
    subsequently to said step of inflating, deflating said balloon permit blood to re-enter the heart.

12. The method defined in claim 11, further comprising the step of periodically inflating said balloon upon completion of said step of inserting.

13. The method defined in claim 12 wherein said balloon is connected at a proximal end to a pressurization device, said step of periodically inflating including the step of operating said pressurization device.

14. The method defined in claim 11, further comprising the step of unfolding said balloon in said intrapericardial space upon insertion of said balloon into said intrapericardial space.

15. The method defined in claim 14 wherein said balloon has an arcuate cuff configuration in an inflated configuration, further comprising the step of placing said balloon at least partially around the heart in said intrapericardial space upon completion of said step of inserting.

16. A surgical method for resuscitating a stopped heart, comprising the steps of:
    providing a hypodermic type needle with a dilating device;
    further providing en inflatable balloon in a collapsed configuration;
    partially inserting said needle with said dilating device into an intrapericardial space about a stopped heart;
    removing said needle from the intrapericardial space while maintaining a distal end portion of said dilating device in said intrapericardial space;
    upon disposition of said distal end portion of said dilating device in said intrapericardial space, expanding said dilating device;
    inserting said balloon in said collapsed configuration into said intrapericardial space through the expanded dilating device;
    inflating the unfolded balloon in said intrapericardial space to place a compressive pressure on the stopped heart sufficient to force blood from the heart; and
    subsequently to said step of inflating, deflating said balloon to permit blood to re-enter the heart.

17. The method defined in claim 16, further comprising the step of unfolding said balloon in said intrapericardial space upon insertion of said balloon into said intrapericardial space.

18. The method defined in claim 16, further comprising the step of periodically inflating said balloon upon completion of said step of inserting.

19. The method defined in claim 18 wherein said balloon is connected at a proximal end to a pressurization device, said step of periodically inflating including the step of operating said pressurization device.

20. The method defined in claim 16, further comprising the step of unfolding said balloon in said intrapericardial space upon insertion of said balloon into said intrapericardial space.

21. The method defined in claim 20 wherein said balloon has an arcuate cuff configuration in an inflated configuration, further comprising the step of placing said balloon at least partially around the heart in said intrapericardial space upon completion of said step of inserting.

* * * * *

UNITED STATES PATENT AND TRADEMARK OFFICE
CERTIFICATE OF CORRECTION

PATENT NO. : 5,385,528
DATED : January 31, 1995
INVENTOR(S) : Peter J. Wilk

It is certified that error appears in the above-indentified patent and that said Letters Patent is hereby corrected as shown below:

Column 5, line 10, claim 1, change "no" to --to--.

Column 6, line 14, claim 11, insert --to-- after "balloon"; line 36, claim 16, change "en" to --an--.

Signed and Sealed this

Eighteenth Day of April, 1995

Attest:

BRUCE LEHMAN

*Commissioner of Patents and Trademarks*

*Attesting Officer*